(12) United States Patent
Khan

(10) Patent No.: US 11,191,981 B2
(45) Date of Patent: Dec. 7, 2021

(54) ANHYDROUS DENTIFRICE

(71) Applicant: GlaxoSmithKline Consumer Healthcare (UK) IP Limited, Brentford (GB)

(72) Inventor: Shazada Yassar Khan, Brentford (GB)

(73) Assignee: GlaxoSmithKline Consumer Healthcare (UK) IP Limited, Brentford (GB)

( * ) Notice: Subject to any disclaimer, the term of this patent is extended or adjusted under 35 U.S.C. 154(b) by 0 days.

(21) Appl. No.: 16/471,690

(22) PCT Filed: Dec. 18, 2017

(86) PCT No.: PCT/EP2017/083351
§ 371 (c)(1),
(2) Date: Jun. 20, 2019

(87) PCT Pub. No.: WO2018/114825
PCT Pub. Date: Jun. 28, 2018

(65) Prior Publication Data
US 2019/0314647 A1 Oct. 17, 2019

(30) Foreign Application Priority Data
Dec. 20, 2016 (GB) ..................... 1621685

(51) Int. Cl.
*A61Q 11/02* (2006.01)
*A61K 8/36* (2006.01)
*A61K 8/81* (2006.01)
*A61K 8/19* (2006.01)
*A61K 8/34* (2006.01)

(52) U.S. Cl.
CPC ............... *A61Q 11/02* (2013.01); *A61K 8/36* (2013.01); *A61K 8/8147* (2013.01); *A61K 8/19* (2013.01); *A61K 8/345* (2013.01); *A61K 2800/31* (2013.01); *A61K 2800/58* (2013.01)

(58) Field of Classification Search
CPC .......... A61Q 11/02; A61Q 11/00; A61K 8/36; A61K 8/8147; A61K 8/19; A61K 8/345; A61K 2800/31; A61K 2800/58
See application file for complete search history.

(56) References Cited

U.S. PATENT DOCUMENTS

| 2004/0047814 A1* | 3/2004 | Xu ........................... A61K 8/24 424/49 |
| 2014/0234383 A1* | 8/2014 | Ashcroft ................ A61K 8/345 424/401 |
| 2016/0213581 A1* | 7/2016 | McGill ................... A61Q 11/00 |
| 2017/0312194 A1* | 11/2017 | Robbins ................... A61K 8/27 |

FOREIGN PATENT DOCUMENTS

| CN | 104 288 466 A | 1/2015 |
| WO | WO 2010/054494 A2 | 5/2010 |

\* cited by examiner

*Primary Examiner* — Snigdha Maewall
(74) *Attorney, Agent, or Firm* — Roshni A. Sitapara

(57) ABSTRACT

Non-aqueous dentifrice compositions comprising an alkaline earth metal acetate salt such as strontium acetate and/or an alkaline earth metal nitrate salt such as strontium nitrate; a carboxyvinyl polymer and a humectant.

8 Claims, 1 Drawing Sheet

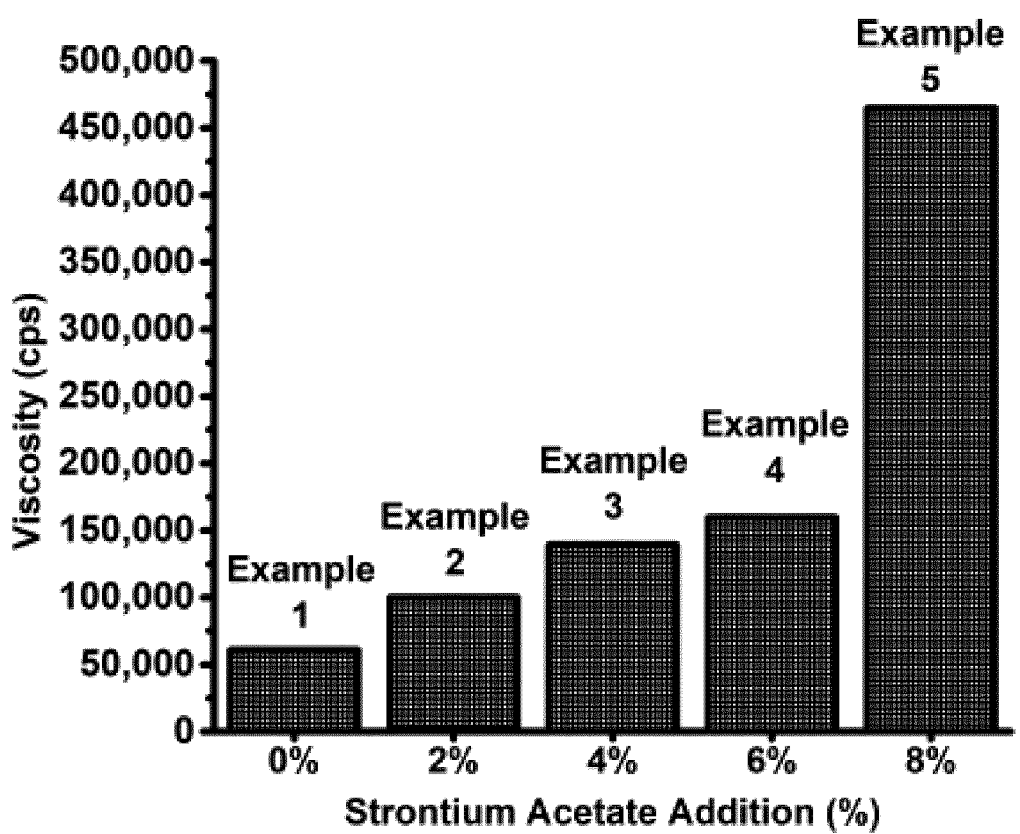

ANHYDROUS DENTIFRICE

This application is a 371 of International Application No. PCT/EP2017/083351, filed 18 Dec. 2017, which claims the priority of GB Application No. GB 1621685.5 filed 20 Dec. 2016, which is incorporated herein in its entirety.

FIELD OF THE INVENTION

The present invention relates to a dentifrice composition, in particular to a non-aqueous (anhydrous) dentifrice composition. A non-aqueous composition according to the invention provides a suitable vehicle or base for use in conjunction with other ingredients desirable in a dentifrice formulation. Such ingredients include those that may be unstable and incompatible in a non-aqueous dentifrice formulation such as potassium nitrate, stannous fluoride or sodium fluoride; and/or those ingredients that are unstable and incompatible in an aqueous-based dentifrice composition such as a bioactive glass. A non-aqueous dentifrice composition according to the invention comprises an alkaline earth metal acetate salt such as strontium acetate and/or an alkaline earth metal nitrate salt such as strontium nitrate; a carboxyvinyl polymer and a humectant.

BACKGROUND OF THE INVENTION

Non-aqueous dentifrice compositions are known in the art and have been suggested as a means of overcoming incompatibility or stability problems that arise with aqueous systems of typical dentifrice compositions.

U.S. Pat. No. 4,988,500 (The Procter & Gamble Company) describes an anhydrous oral composition comprising a carboxyvinyl polymer, a neutralising agent, a peroxide or perborate compound and an anhydrous humectant. It is however necessary to neutralise the carboxyvinyl polymer in order to obtain dentifrice compositions that provide acceptable viscosity characteristics.

U.S. Pat. No. 4,647,451 (Colgate-Palmolive Company) describes an anhydrous dentifrice containing a polysaccharide gum and a glycerine humectant. Polyethylene glycol is optionally added as a dispersion agent.

U.S. Pat. No. 56,700,137 (L'Oreal) describes a dentifrice composition containing an anhydrous medium which comprises glycerine, at least one hydroxyethylcellulose having at least one hydrophobic chain, and at least one pyrogenic silica with an average particle size of less than 40 nm.

U.S. Pat. No. 5,882,630 (SmithKline Beecham) describes an anhydrous dentifrice containing a carboxyvinyl polymer, a humectant, a polyethylene glycol, and an abrasive. Suitable carboxyvinyl polymers described include copolymers of acrylic acid cross-linked with polyallylsucrose, for example Carbopol 974 and 934, Carbopol 974 being preferred.

WO96/03108 (SmithKline Beecham plc) describes a non-aqueous dentifrice composition comprising a hydroxyethyl cellulose polymer, a humectant, a polyethylene glycol and a dentally acceptable abrasive.

Whilst the compositions described in the prior art may go some way to addressing formulation problems encountered with dentifrice compositions, there nevertheless remains a need for alternatives including, for example, the provision of non-aqueous dentifrice compositions that exhibit acceptable rheological properties.

It is an object of the present invention to provide such a composition.

SUMMARY OF THE INVENTION

Accordingly, the present invention provides a non-aqueous dentifrice composition comprising an alkaline earth metal acetate salt and/or an alkaline earth metal nitrate salt, a carboxyvinyl polymer and a humectant.

The present invention is based on the unexpected finding that an alkaline earth metal acetate salt, such as strontium acetate, and/or an alkaline earth metal nitrate salt such as strontium nitrate, helps to stabilize a non-aqueous base comprising a carboxyvinyl polymer and a humectant. Advantageously this finding allows the inclusion of incompatible materials in the composition. A non-aqueous dentifrice composition according to the invention exhibits improved physical stability when compared to a composition without the alkaline earth metal acetate or nitrate salt. Whilst not being bound by theory it is believed that the alkaline earth metal acetate or nitrate together with the carboxyvinyl polymer, collectively serve to thicken humectant material in the composition which helps to maintain the structural integrity of the dentifrice. Unlike other non-aqueous compositions which comprise different salts, such as sodium acetate or potassium acetate, and which have a tendency to become runny either directly following manufacture or later on storage, the non-aqueous dentifrice composition according to the invention, containing an alkaline earth metal acetate and/or an alkaline earth metal nitrate salt, exhibits good consistency and does not exhibit a runny character (and does not develop a runny character on storage). Advantageously the non-aqueous dentifrice composition of the invention has the advantage of a good shelf-life.

The alkaline earth metal acetate and/or nitrate salt(s) appears also to confer the necessary rheological properties required to suspend any solid material, such as an abrasive, present in the composition.

These and other features, aspects and advantages of the invention will become evident to those of skill in the art from a reading of the present disclosure.

BRIEF DESCRIPTION OF THE DRAWINGS

FIG. 1 is a graph showing the effect on viscosity of increasing the amount of strontium acetate in a non-aqueous composition according to the invention.

DETAILED DESCRIPTION OF THE INVENTION

The term "dentifrice composition", as used herein means a paste or gel formulation, unless otherwise specified.

As used herein the word "comprising" includes its normal meaning (i.e. includes all the specifically mentioned features as well optional, additional, or unspecified ones), and also includes "consisting of" and "consisting essentially of".

As used herein, the word "about", when applied to a value for a parameter of a composition indicates that the calculation or measurement of the value allows some slight imprecision without having a substantial effect on the chemical or physical attributes of the composition.

A dentifrice composition of the present invention is non-aqueous i.e. is substantially free of any water. This is achieved by not adding water to the composition, by not using an aqueous carrier(s) and, where possible, by avoiding the use of components in their hydrated form. Suitably a component selected for use in the composition will be in its anhydrous form. Whilst recognizing that individual components of the composition may contain limited amounts of free and/or bound water, it is essential that the overall composition remains substantially free of any water. Aqueous carriers of the type commonly used in dentifrice compositions are avoided in the present invention; these include for example aqueous solutions of sodium lauryl sulphate, aqueous solutions of sodium hydroxide and aqueous solutions of colouring agents.

The total amount of water (both free and bound water) in a composition of the invention is kept to a minimum. Suitably a composition of the invention will comprise less than 0.5% water by weight of the composition, suitably less than 0.2% water by weight of the composition, and even more suitably is 0.0% water by weight of the composition.

A composition according to the invention comprises an alkaline earth metal acetate or nitrate salt or a combination thereof. The alkaline earth metal acetate or nitrate salt of use in the invention will have sufficient solubility to deliver the earth metal ions to the composition.

In one aspect the alkaline earth metal nitrate salt is strontium nitrate, zinc nitrate, calcium nitrate or a combination of two or more thereof. In one aspect the alkaline earth metal nitrate salt is strontium nitrate.

In one aspect the alkaline earth metal acetate salt is strontium acetate, zinc acetate, calcium acetate or a combination of two or more thereof. In one aspect the alkaline earth metal acetate is strontium acetate.

Strontium acetate is known in the art as a tubule occluding agent, for use in the treatment of dentine hypersensitivity, and is typically formulated in aqueous-based dentifrice formulations. However its use in the present invention (along with that of the other acetate and nitrate salts of use in the invention), is primarily as a thickening or crosslinking agent. Whilst not being bound by theory, the alkaline earth metal acetate and/or nitrate salt(s), together with the carboxyvinyl polymer, serve to thicken the humectant component and to stabilize the non-aqueous composition.

The alkaline earth metal acetate and/or nitrate salt(s) are present in an amount ranging from about 1% to about 15% by weight of the composition, suitably from about 1.5% to about 10% by weight of the composition, more suitably about 2% to about 8% by weight of the composition. Most suitably the alkaline earth metal acetate and/or nitrate salt(s) is present in an amount less than 8% by weight of the composition, for example from about 2% to about 6% by weight of the composition.

A composition according to the invention comprises a carboxyvinyl polymer. Suitable carboxyvinyl polymers for use in a dentifrice composition of the invention include copolymers of acrylic acid cross-linked with polyallylsucrose, for example Carbopol 974 and 934 or cross-linked with divinyl glycol, for example Noveon AA-1.

Carbopol polymers are manufactured by B.F. Goodrich Company. In one embodiment the carboxyvinyl polymer is Carbopol 974. The carboxyvinyl polymer may be present in an amount ranging from about 0.1% to about 7.5% by weight of the composition, suitably from about 0.3% to about 1.0%, more suitably about 0.85% by weight of the composition.

A composition according to the invention comprises a humectant. Suitable humectants for use in the present invention include glycerine, sorbitol and propylene glycol or mixtures thereof. In one embodiment the humectant is glycerine. It is well known that commercially available glycerine may contain between about 0.5 to about 2.0% by weight of water which is in association with the glycerine. Typically this amount is between about 0.5 to about 1.0% by weight. This small amount of water is bound to the glycerine and is therefore not available to the other ingredients. The skilled person would still consider a composition containing glycerine as being non-aqueous. The humectant should in any case be as anhydrous as possible and preferably used in solid form. As the humectant is used to make the formulations up to 100%, the humectant may be present in the range of from about 20% to about 90% by weight of the dentifrice composition. Suitably the humectant is present from about 35% to about 75% by weight of the composition, more suitably from about 45% to about 70% by weight of the dentifrice composition.

Suitably a composition of the invention comprises a polyethylene glycol. The polyethylene glycol is selected so that it will reduce any stickiness from the formulation and give a smooth textured product. Suitably, the polyethylene glycol is selected from PEG 300 and PEG 400. In one embodiment the polyethylene glycol is PEG 400.

Advantageously, the polyethylene glycol is present in an amount ranging from about 0.1% to about 40% by weight of the composition, suitably from about 15% to about 25% by weight of the dentifrice composition.

In a further aspect the dentifrice composition of the present invention further comprises a material that is unstable or incompatible with an aqueous environment. An example of such a material is a bioactive silica-based glass of the type disclosed in WO 96/10985, WO 97/27158 and WO 99/13852. In an aqueous environment such a bioactive glass releases ions causing a significant increase in pH which can adversely affect the stability (especially upon long term storage) of any excipients contained within the dentifrice. Formulating a bioactive silica-based glass in the anhydrous dentifrice of the present invention prevents the release of ions within the dentifrice thereby controlling the pH and increasing the long-term storage stability of the dentifrice.

In a further aspect the dentifrice composition of the present invention comprises one or more materials that may be unstable and incompatible in a non-aqueous dentifrice composition, for example as in a composition according to comparative Example 1 herein in the absence of an alkaline earth metal acetate or nitrate salt. These may include, for example, potassium nitrate or an alkali metal fluoride salt such as sodium fluoride or stannous fluoride, and combinations thereof.

Suitably a composition according to the invention comprises an abrasive. Abrasives for use in the present invention include, for example, silica, zinc orthophosphate, sodium bicarbonate (baking soda), plastic particles, alumina, hydrated alumina, calcium carbonate and calcium pyrophosphate or mixtures thereof.

Suitably the abrasive is a silica abrasive. Suitably the silica abrasive is a natural amorphous silica, for instance diatomaceous earth; or a synthetic amorphous silica such as a precipitated silica, for instance 'Tixosil 53B', manufactured by Rhone Poulenc, or a silica gel, such as a silica xerogel; or mixtures thereof.

Generally, an amount of abrasive suitable for use in the dentifrice composition of the present invention will be empirically determined to provide an acceptable level of cleaning and polishing, in accordance with the techniques well known in the art. Suitably, the abrasive will be present in an amount from about 1% to about 60% by weight of the composition, suitably from about 2% to about 30% by weight of the composition or from about 3% to about 10%, by weight of the composition.

In one aspect a composition according to the invention comprises a thickening agent. Suitably the thickening agent is a thickening silica, such as Sident 22S, which is manufactured by Degussa Ltd. Suitably the thickening agent will be present in an amount from about 0.01 to about 20% by weight of the composition, suitably from about 5% to about 15% by weight of the composition.

In one aspect a composition according to the invention comprises a thickening silica. In one aspect a composition according to the invention is essentially free of any further/additional thickening agent(s).

Surfactant materials are usually added to dentifrice products to provide cleaning and/or foaming properties. Any conventional surfactant used in dentifrice formulations may be used in the present invention, provided that it can be added as a solid powder, that is not in an aqueous solution.

Suitable surfactants include anionic, cationic, nonionic and amphoteric surfactants.

Suitable nonionic surfactants include, for example polyethoxylated sorbitol esters, in particular polyethoxylated sorbitol monoesters, for instance, PEG(40) sorbitan diisostearate, and the products marketed under the trade name 'Tween' by ICI; polycondensates of ethylene oxide and propylene oxide (poloxamers), for instance the products marketed under the trade name 'Pluronic' by BASF-Wyandotte; condensates of propylene glycol; polyethoxylated hydrogenated castor oil, for instance, cremophors; and sorbitan fatty esters.

Suitable anionic surfactants include, for example sodium lauryl sulphate, marketed by Albright and Wilson and known as 'SLS'. This may be obtained and is used in a powder form in the present invention. A further suitable anionic surfactant is sodium methyl cocyl taurate, marketed under the trade name 'Adinol CT 95' manufactured by Croda chemicals.

Suitable amphoteric surfactants include, for example a betaine. Structurally, betaine compounds contain an anionic functional group such as a carboxylate functional group and a cationic functional group such as quaternary nitrogen functional group separated by a methylene moiety. They include n-alkyl betaines such as cetyl betaine and behenyl betaine, and n-alkylamido betaines such as cocoamidopropyl betaine. In one embodiment the betaine is cocoamidopropyl betaine, commercially available under the trade name Tego Betain.

Advantageously, the surfactant is present in an amount ranging from about 0.005% to about 20% by weight of the composition, suitably from about 0.1% to about 10% by weight of the composition, more suitably 0.1% to 5% by weight of the composition.

Advantageously a dentifrice according to the invention may further comprise an ionic fluorine-containing compound, which may include ionic fluorides, such as alkali metal fluorides, amine fluorides and ionic monofluorophosphates, such as alkali metal monofluorophosphates, and which may be incorporated into the formulation, to provide between 100 and 3000 ppm, preferably 500 to 2000 ppm of fluoride. Preferably the ionic fluoride or monofluorophosphate is an alkali metal fluoride or monofluorophosphate, for instance sodium fluoride or sodium monofluorophosphate, respectively.

It will further be appreciated that if an ionic fluoride-containing compound is incorporated in a dentifrice of the invention, the abrasive should be chosen so that it is compatible with the ionic fluorine-containing compound.

Dentifrices according to the invention may also contain other agents conventionally used in dentifrice formulations, for example colouring agents, whitening agents, for example titanium dioxide; preservatives and sweetening agents. Anti-plaque agents, for example triclosan, chlorhexidine, or cetyl pyridinium chloride, or anti-calculus agents, for example pyrophosphate salts, anti-sensitivity agents, for example strontium or potassium salts e.g. potassium nitrate. Suitably potassium nitrate may be present in an amount ranging from about 3 to about 10% by weight of the composition, more suitably about 5% by weight of the composition. Breath freshening agents, for example, sodium bicarbonate and tooth whitening agents, for example hydrogen peroxide and sodium tripolyphosphate may also be included at appropriate levels.

In general, such agents will be in a minor amount or proportion of the composition, usually present in an amount ranging from about 0.001% to about 5% by weight of the composition. In one embodiment sodium tripolyphosphate is present in an amount of about 5% by weight of the composition. Because of the inventive combination of ingredients used in the present invention, any active ingredient or combination of actives that are unstable or incompatible in any way with aqueous (or with non-aqueous) environments may also be added to the composition of the present invention. Flavouring agents may also be added to the compositions, usually at a typical level of about 1.0% by weight of the composition.

Suitable sweetening agents include saccharin, cyclamate and acesulfame K, and may be present in from about 0.01% to about 0.5%, suitably from about 0.05% to about 0.5% by weight of the composition. An auxiliary sweetener such as a thaumatin may also be included, at a level of from about 0.001% to about 0.1%, suitably from about 0.005% to about 0.05% by weight of the composition. A suitable blend of thaumatins is marketed under the trade name 'TALIN' by Tate and Lyle plc.

Dentifrices according to the invention may also contain an antistain agent. Suitable antistain agents include, for example, carboxylic acids such as those disclosed in U.S. Pat. No. 4,256,731, amino carboxylate compounds such as those disclosed in U.S. Pat. No. 4,080,441, phosphonoacetic acid, as disclosed in U.S. Pat. No. 4,118,474, or polyvinylpyrrolidone as disclosed in WO 93/16681. The antistain agent may be incorporated into the dentifrice composition or may be provided as a separate composition, for use after the dentifrice.

The pH of the formulation when diluted in the ratio of 3:1 with water should suitably be less than 10.0.

Suitably a dentifrice composition according to the invention will have a viscosity at 25° C. of greater than 75,000 cps, suitably from about 80,000 to about 500,000 cps, such as from about 90,000 cps to about 140,000 cps, which is necessary for producing a product that is comparable to conventional dentifrices that have consumer acceptability. The viscosity of the dentifrice may be measured using a TF 20 spindle Brookfield Viscometer. Suitably a Brookfield RVT or equivalent digital viscometer may be used utilizing a TF spindle at 20 rpm for 1 minute, helipath on, at 25+/−2° C.

A composition according to the invention may be prepared in the conventional manner by mixing the alkaline earth metal acetate and/or nitrate, with the humectant, carboxyvinyl polymer and the polyethylene glycol (when present). Other ingredients of the composition may then be added in the required proportions and in any order which is convenient and thereafter and if necessary, the pH may be adjusted.

The following Examples illustrate the invention.

Examples 1-5 (Dentifrice Compositions)

| Ingredient | Example 1* % w/w | Example 2 % w/w | Example 3 % w/w | Example 4 % w/w | Example 5 % w/w |
|---|---|---|---|---|---|
| Glycerol | 53.0648 | 50.8348 | 48.6048 | 46.3748 | 44.1448 |
| Polyethylene Glycol | 20.0000 | 20.0000 | 20.0000 | 20.0000 | 20.0000 |
| Thickening Silica | 10.0000 | 10.0000 | 10.0000 | 10.0000 | 10.0000 |
| Abrasive Silica | 6.0000 | 6.0000 | 6.0000 | 6.0000 | 6.0000 |
| Potassium Nitrate | 5.0000 | 5.0000 | 5.0000 | 5.0000 | 5.0000 |
| Sodium Fluoride | 0.3152 | 0.3152 | 0.3152 | 0.3152 | 0.3152 |
| Titanium Dioxide | 1.0000 | 1.0000 | 1.0000 | 1.0000 | 1.0000 |
| Carbopol 974P | 0.8400 | 0.8400 | 0.8400 | 0.8400 | 0.8400 |
| Flavour | 1.0300 | 1.0300 | 1.0300 | 1.0300 | 1.0300 |
| Cocamidopropyl Betaine | 1.2000 | 1.2000 | 1.2000 | 1.2000 | 1.2000 |
| Sodium Methyl Cocoyl Taurate | 1.2000 | 1.2000 | 1.2000 | 1.2000 | 1.2000 |
| Saccharin Sodium | 0.3500 | 0.3500 | 0.3500 | 0.3500 | 0.3500 |
| Strontium Acetate | | 2.0000 | 4.0000 | 6.0000 | 8.0000 |
| Sodium hydroxide anhydrous powder | | 0.2300 | 0.4600 | 0.6900 | 0.9200 |
| Total | 100.0000 | 100.0000 | 100.0000 | 100.0000 | 100.0000 |

*not a composition of the invention; included for comparative purposes.

Example 6—Viscosity Determination

Methodology

The viscosity of dentifrice compositions as described in Examples 1-5 was determined one week after manufacture, using a TF 20 spindle Brookfield Visocometer.

A sample of the paste, sufficient to fill a cylindrical container of minimum internal diameter of 60 mm to a minimum depth of 60 mm was used; typically the sample size was about 500-600 ml. The spindle was brought down to the sample surface and the measurement taken with the helical motor switched on. Scale readings were taken when the viscometer had reached steady state and the scale value was constant.

Results

The viscosity measurements are shown in FIG. 1. The results demonstrate that viscosity of the compositions was increased in the presence of strontium acetate in a dose-dependent manner.

Conclusion

The data indicate that an anhydrous composition comprising potassium nitrate and sodium fluoride in the absence of strontium acetate (Example 1) exhibited a significantly lower viscosity compared to compositions comprising strontium acetate (Examples 2-5). Whilst not being bound by theory, strontium acetate serves to thicken and hence stabilize compositions (such as those described in Examples 2-5) which contain materials such as potassium nitrate (and/or sodium fluoride) and which otherwise may be incompatible with a polyacrylic acid (carbopol)—containing anhydrous base present in the composition. A dentifrice composition according to Example 1, having a viscosity below 75000 cps, is generally seen as less desirable, from an appearance and consumer acceptability perspective.

Examples 7-10 (Dentifrice Compositions)

| Ingredient | Example 7 % w/w | Example 8 % w/w | Example 9 % w/w | Example 10 % w/w |
|---|---|---|---|---|
| Glycerol | 51.15 | 51.96 | 50.88 | 51.33 |
| Macrogol 400 | 20.00 | 20.00 | 20.00 | 20.00 |
| Thickening Silica | 8.40 | 8.40 | 8.40 | 8.40 |
| Abrasive Silica | 6.00 | 6.00 | 6.00 | 6.00 |
| Sodium Tripolyphosphate Anhydr (STP-188) | 5.00 | 5.00 | 5.00 | 5.00 |
| Flavour | 1.20 | 1.20 | 1.20 | 1.20 |
| Sodium Lauryl Sulfate | 1.10 | 1.10 | 1.10 | 1.10 |
| Titanium Dioxide | 1.00 | 1.00 | 1.00 | 1.00 |
| Carbopol 974P | 0.84 | 0.84 | 0.84 | 0.84 |
| Sodium Saccharin | 0.50 | 0.50 | 0.50 | 0.50 |
| Stannous Fluoride | 0.45 | 0.45 | 0.45 | 0.45 |
| Cocamidopropyl Betaine (TEGO Betain CK D) | 0.36 | 0.36 | 0.36 | 0.36 |
| Strontium Acetate[Sr(OAc)2] | 4.00 | | | |
| Sodium Acteate [Na(OAc)$_2$] | | 3.19 | | |
| Zinc Acetate [Zn(OAc)2] | | | 4.27 | |
| Potassium Acetate [K(OAc)$_2$] | | | | 3.82 |
| Total | 100.00 | 100.00 | 100.00 | 100.00 |

Examples 8 and 10 are not compositions of the invention and are included herein for comparative purposes only.

Example 11—Viscosity Determination

Methodology

The viscosity of dentifrice compositions according to Examples 7-10 was determined. The same methodology as used in Example 6 was used.

Results

The composition of Example 7 containing Sr(OAc)$_2$ showed the highest viscosity (119,000 cps) whilst the composition of Example 9 containing Zn(OAc)$_2$ showed a reasonable viscosity (77,500 cps). The compositions of Examples 8 and 10, containing respectively Na(OAc)$_2$ and K(OAc)$_2$ exhibited significantly lower viscosities (25,000 and 37,000 cps respectively) and fall outside the scope of the present invention.

Conclusion

The data indicate that anhydrous compositions comprising stannous fluoride and strontium acetate or zinc acetate (Examples 7 and 9) exhibited significantly higher viscosities compared to similar compositions comprising either sodium or potassium acetate (Examples 8 and 10). Whilst not being bound by theory the presence of strontium acetate or zinc acetate served to thicken and hence stabilize compositions whereas the same advantageous effect was not observed with either sodium or potassium acetate.

Examples 12-14 (Dentifrice Compositions)

| Ingredient | Example 12 %w/w | Example 13* %w/w | Example 14 %w/w |
|---|---|---|---|
| Glycerol | 51.1460 | 51.5744 | 51.0309 |
| Macrogol 400 | 20.0000 | 20.0000 | 20.0000 |
| Thickening Silica | 8.4000 | 8.4000 | 8.4000 |
| Abrasive Silica | 6.0000 | 6.0000 | 6.0000 |
| Sodium Tripolyphosphate Anhydrous (STP-188) | 5.0000 | 5.0000 | 5.0000 |
| Flavour | 1.2000 | 1.2000 | 1.2000 |
| Sodium Lauryl Sulfate | 1.1000 | 1.1000 | 1.1000 |
| Titanium Dioxide | 1.0000 | 1.0000 | 1.0000 |
| Carbomer Homopolymer (Carbopol 974P) | 0.8400 | 0.8400 | 0.8400 |
| Sodium Saccharin | 0.5000 | 0.5000 | 0.5000 |
| Stannous Fluoride | 0.4540 | 0.4540 | 0.4540 |
| Cocamidopropyl Betaine (TEGO Betain CK D) | 0.3600 | 0.3600 | 0.3600 |
| Strontium Acetate [$Sr(AOc)_2$] | 4.0000 | | |
| Strontium Sulphate[$SrSO_4$] | | 3.5716 | |
| Strontium Nitrate[$Sr(NO_3)_2$] | | | 4.1151 |
| Total | 100.0000 | 100.0000 | 100.0000 |
| Viscosity[cPs] | 121000 | 30000 | 122000 |

*not a composition of the invention; included for comparative purposes.

Example 15—Viscosity Determination

Methodology

The viscosity of dentifrice compositions according to Examples 12-14 was determined. The same methodology as used in Example 6 was used.

Results

The composition of Examples 12 and 14 containing $Sr(OAc)_2$ and $Sr(NO_3)_2$ exhibited a high viscosity, specifically 121000 cps and 122000 respectively, whilst the composition of Example 13 containing $SrSO_4$ exhibited a significantly lower viscosity reasonable viscosity (30000 cps) and so falls outside the scope of the present invention.

Conclusions

The presence of strontium acetate or strontium nitrate served to thicken and hence stabilize the compositions whereas strontium sulphate appeared to have the opposite effect of destabilizing the composition.

Whilst not being bound by theory, the soluble forms of strontium, such as $Sr(NO_3)_2$ and $Sr(OAc)_2$, dissolve in glycerol to free strontium ions so that they may crosslink the carboxyvinyl polymer, whereas $SrSO_4$ is not soluble and does not have free strontium to crosslink the carboxyvinyl polymer.

The invention claimed is:

1. A non-aqueous dentifrice composition comprising a source of fluoride ions sufficient to provide 500 to 2000 ppm fluoride; 2% to 8% by weight of an alkaline earth metal acetate salt and/or an alkaline earth metal nitrate salt; 0.3% to 1.0% by weight a carboxyvinyl polymer; 35% to 75% by weight of a humectant selected from the group consisting of glycerine, sorbitol, propylene glycol and mixtures thereof; and an abrasive,
wherein the carboxyvinyl polymer is a copolymer of an acrylic acid crosslinked with polyallylsucrose or divinylglycol, and
wherein the composition comprises a viscosity at 25° C. of from about 90,000 cps to about 140,000 cps.

2. A non-aqueous dentifrice composition according to claim 1 wherein the alkaline earth metal acetate salt is strontium acetate, zinc acetate, calcium acetate or a combination of two or more thereof.

3. A non-aqueous dentifrice composition according to claim 2 wherein the alkaline earth metal acetate salt is strontium acetate.

4. A non-aqueous dentifrice composition according to claim 1 wherein the alkaline earth metal nitrate salt is strontium nitrate, zinc nitrate, calcium nitrate or a combination of two or more thereof.

5. A non-aqueous dentifrice composition according to claim 4 wherein the alkaline earth metal nitrate is strontium nitrate.

6. A non-aqueous dentifrice composition according to claim 1 wherein the humectant is glycerine, sorbitol or propylene glycol.

7. A non-aqueous dentifrice composition according to claim 1 wherein the humectant is glycerine.

8. A non-aqueous dentifrice composition according to claim 1 further comprising polyethylene glycol.

* * * * *